US007927350B2

(12) United States Patent
Rabbitte et al.

(10) Patent No.: US 7,927,350 B2
(45) Date of Patent: Apr. 19, 2011

(54) PLAQUE LIBERATING DEVICE

(75) Inventors: Gerard Rabbitte, Tuam (IE); Ronald Kelly, Oranmore (IE)

(73) Assignee: Salviac Limited, Dublin (IE)

( * ) Notice: Subject to any disclaimer, the term of this patent is extended or adjusted under 35 U.S.C. 154(b) by 160 days.

(21) Appl. No.: 12/211,253

(22) Filed: Sep. 16, 2008

(65) Prior Publication Data
US 2010/0069826 A1    Mar. 18, 2010

(51) Int. Cl.
*A61M 29/00*    (2006.01)
(52) U.S. Cl. .................................. 606/200; 604/500
(58) Field of Classification Search .............. 606/108, 606/159, 191–194, 200; 604/19, 22, 93.01, 604/104, 500; 623/1.11
See application file for complete search history.

(56) References Cited

U.S. PATENT DOCUMENTS

| 4,723,549 | A | 2/1988 | Wholey et al. |
| 5,053,008 | A | 10/1991 | Bajaj |
| 5,108,419 | A | 4/1992 | Reger et al. |
| 6,336,934 | B1 | 1/2002 | Gilson et al. |
| 6,575,996 | B1 | 6/2003 | Denison et al. |
| 6,695,813 | B1 | 2/2004 | Boyle et al. |
| 6,852,116 | B2 * | 2/2005 | Leonhardt et al. ............ 606/108 |
| 7,097,440 | B2 | 8/2006 | Papp et al. |
| 7,172,621 | B2 * | 2/2007 | Theron .................... 623/1.11 |
| 2007/0213753 | A1 | 9/2007 | Waller |

FOREIGN PATENT DOCUMENTS

| WO | 98/33443 A1 | 8/1998 |
| WO | WO 2007/103167 A1 | 9/2007 |

* cited by examiner

*Primary Examiner* — Michael J Milano
*Assistant Examiner* — Victor X Nguyen
(74) *Attorney, Agent, or Firm* — Sughrue Mion, PLLC; Jonathan Feuchtwang

(57) ABSTRACT

A device and method for liberating plaque from a lumen after a medical procedure has been formed. The device includes a catheter having a first expandable member and a second expandable member.

23 Claims, 6 Drawing Sheets

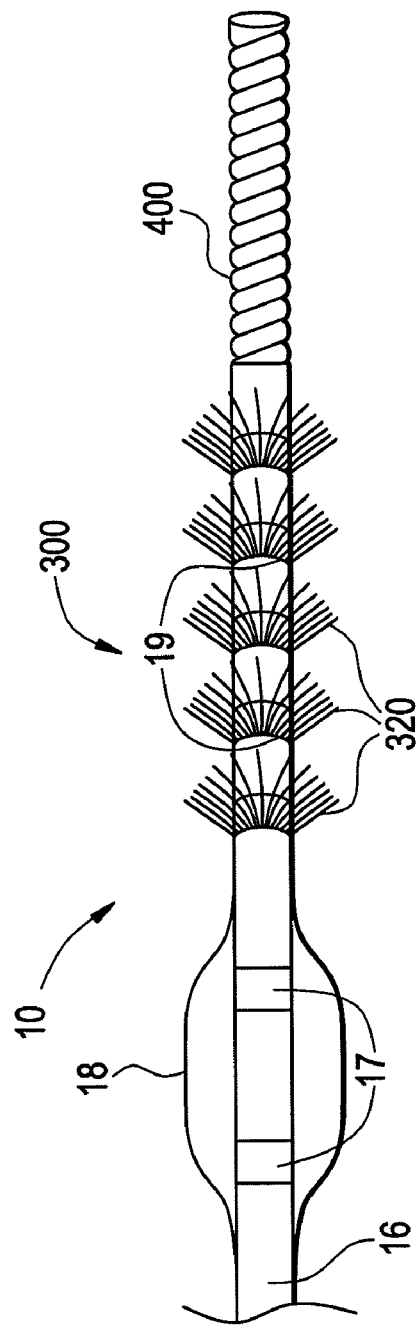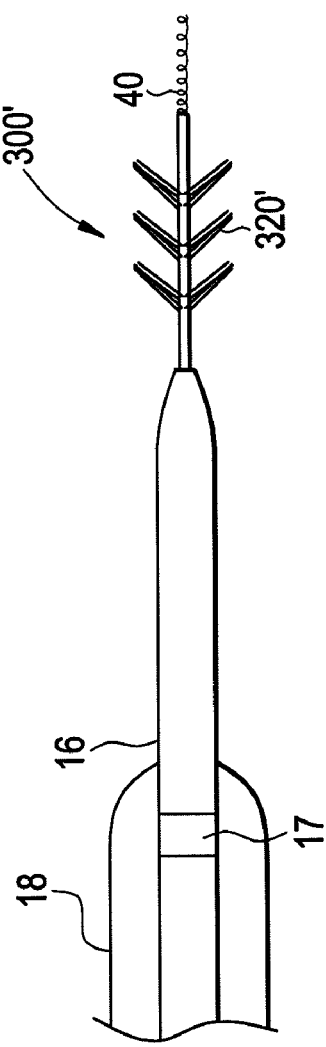

PLAQUE LIBERATING DEVICE

FIELD OF THE INVENTION

The present invention relates generally to medical devices, and more particular to devices and methods for preventing late embolic events following angioplasty or stenting.

BACKGROUND OF THE INVENTION

The term "STROKE" is used to describe a medical event whereby blood supply to the brain or specific areas of the brain is restricted or blocked to the extent that the supply is inadequate to provide the required flow of oxygenated blood to maintain function. The brain will be impaired either temporarily or permanently, with the patient experiencing a loss of function such as sight, speech or control of limbs. There are two distinct types of stroke, hemorrhagic and embolic. Embolic stroke may be caused by embolic material that may become dislodged after stenting.

Medical literature describes artery disease as a significant source of embolic material. Typically, an atherosclerotic plaque builds up in the arteries. The nature of the plaque varies considerably, but in a significant number of cases pieces of the plaque can break away and flow distally and, for example, block blood flow to specific areas of the brain and cause neurological impairment, plaque can also break free and flow into the lungs or heart and cause other adverse events. Treatment of the disease in the carotid artery is classically by way of surgical carotid endarterectomy whereby, the carotid artery is cut and the plaque is physically removed from the vessel. The procedure has broad acceptance with neurological complication rates quoted as being low, somewhere in the order of 5% although claims vary widely on this.

Not all patients are candidates for surgery. A number of reasons may exist such that the patients could not tolerate surgical intervention. In these cases and in an increasing number of candidates that are surgical candidates are being treated using transcatheter techniques. In this case, the evolving approach uses devices inserted in the femoral artery and manipulated to the site of the stenosis. A balloon angioplasty catheter is inflated to open the artery and an intravascular stent is sometimes deployed at the site of the stenosis. The action of these devices as with surgery can dislodge embolic material which will flow with the arterial blood and if large enough, eventually block a blood vessel and cause a stroke.

It is known to permanently implant a filter in human vasculature, such as the vena cava, to catch embolic material. It is also known to use a removable filter for this purpose. Such removable filters typically comprise umbrella type filters comprising a filter membrane supported on a collapsible frame on a guidewire for movement of the filter membrane between a collapsed position against the guidewire and a laterally extending position occluding a vessel. Examples of such filters are shown in U.S. Pat. No. 4,723,549, U.S. Pat. No. 5,053,008, U.S. Pat. No. 5,108,419 and WO 98/33443. Various deployment and/or collapsing arrangements are provided for the umbrella filter.

Improved filter devices have been designed to overcome the shortcomings of the previous filters. For example, in one embodiment, the filter is freely disposed along the length to the guidewire, thereby allowing the guidewire to be moved independently of the filter assembly.

After the filter has crossed the stenosed region of the vessel, the filter is deployed within the vessel to capture any emboli that may be dislodged during subsequent medical procedure(s).

One example of a subsequent medical procedure that may be performed is percutaneous transluminal coronary angioplasty (PTCA). PTCA is a procedure for treating vascular disease. This procedure generally entails introducing a balloon catheter assembly into the vascular system of a patient via the brachial or femoral artery and advancing the balloon catheter assembly through the vasculature until the balloon is positioned across an occlusive lesion. Once in position across the lesion, the balloon is inflated to a predetermined size to radially compress against the plaque of the lesion to remodel the vessel wall. Subsequently, the balloon is deflated to allow the balloon catheter assembly to be withdrawn from the vasculature.

Typically after PTCA, a stent may be in the lumen to maintain the vascular patency. Additionally, to better effectuate the treatment of such vascular disease, it may be preferable to load an intraluminal device or prosthesis with one or more beneficial agents, such as antiproliferatives, for delivery to a lumen. One commonly applied technique for the local delivery of a drug is the use of a polymeric carrier coated onto the surface of a stent. Such conventional methods and products generally have been considered satisfactory for their intended purpose.

The stent may be constructed to be a self-expanding stent, whereby the stent expands to support the vessel when a restraining sheath is removed or a balloon expanadable stent, which is expanded by inflating a balloon on which the stent is mounted or crimped around. In either instance, stents are constructed having multiple struts creating scaffolding for the vessel. While the struts of the stent support the vessel, the open areas between the struts do not support the vessel or the plaque. In many instances plaque extrudes between the struts in to the open areas of the stent, the extruded plaque may eventually break free and form emboli within the vessel which may cause a stroke.

Therefore, there is a need for a device and method of use for reducing emboli due to this extruded plaque.

BRIEF SUMMARY

In accordance with the present invention there is provided a catheter for reducing emboli formation after a medical procedure, comprising: a generally elongate shaft member having a proximal end and a distal end; a first expandable member movable between a first collapsed position and a second expanded position, the first expandable member associated with the elongated shaft member, the first expandable member disposed proximal to the distal end of the shaft member; a second expandable member movable between a first collapsed position and a second expanded position, the second expandable member associated with the elongated shaft, the second expandable member disposed between the first expandable member and the distal end of the shaft; and a sheath disposed at least partially about the second expandable member.

In accordance with the present invention there is provided a method for reducing emboli formation, including the steps of: (1) inserting an embolic protection device within a lumen distal to an area of treatment, the embolic protection device including a guidewire; (2) expanding the embolic protection device from a collapsed configuration to an expanded configuration; (3) passing a medical device over the guidewire and performing a medical procedure in the area of treatment within the lumen adjacent to the embolic protection device; (4) removing the medical device from the guidewire; (5) passing a catheter over the guidewire, the catheter including first and second expandable members associated with the catheter, expanding the first expandable member thereby causing the second expandable member to expand; (6) unexpanding the first expandable member and moving the catheter proximally from the area of treatment, thereby causing material extending into the vessel to be removed by the expanded second expandable member; and (7) retrieving the embolic protection device from the lumen.

It is to be understood that both the foregoing general description and the following detailed description are exemplary and are intended to provide further explanation of the invention claimed.

The accompanying figures, which are incorporated in and constitute part of this specification, are included to illustrate and provide a further understanding of the method and system of the invention. Together with the description, the figures serve to explain the principles of the invention.

BRIEF DESCRIPTION OF THE DRAWINGS

In order to describe the manner in which the above-recited and other advantages and features of the invention can be obtained, a more particular description of the invention briefly described above will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings.

FIG. 2E is an enlarged view of the distal end portion of the catheter in accordance with the present invention illustrating another alternative embodiment of the second expandable member.

FIG. 2F is an enlarged view of the distal end portion of the catheter in accordance with the present invention illustrating another alternative embodiment of the second expandable member.

Figure 1:
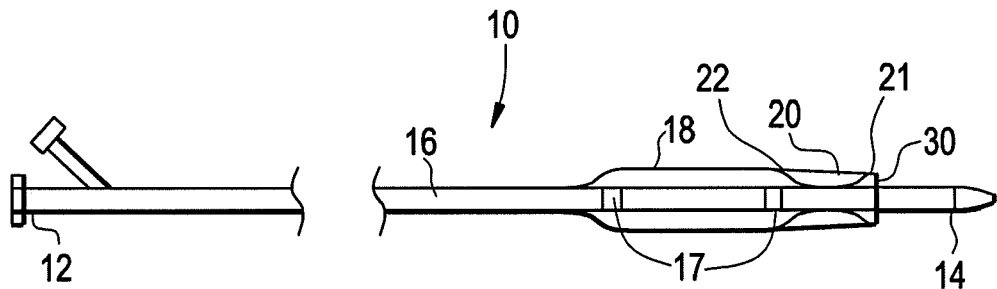
FIG. 1 is a plan view of an exemplary embodiment of the emboli reducing catheter in accordance with the present invention.

It should be noted that the figures are not drawn to scale and that elements of similar structures or functions are generally represented by like reference numerals for illustrative purposes throughout the figures. It also should be noted that the figures are only intended to facilitate the description of embodiments of the present invention.

DETAILED DESCRIPTION

In accordance with the present invention herein, there is provided devices and methods for reducing emboli formation following a medical procedure. In accordance with one embodiment of the present invention there is provided a catheter assembly comprising a shaft, a first expandable member disposed about the shaft, a second expandable member and a tip.

Referring now to FIG. 1, there is shown an exemplary embodiment of a catheter 10 in accordance with the present invention. As shown in FIG. 1, the catheter 10 includes an elongated shaft 16 having a proximal end 12 and a distal end 14. At least one lumen (not shown) extends through the length of the shaft 16. The shaft 16 may be composed of multiple components, such as an inner member and an outer member arranged in a coaxial or side-by-side configuration, wherein the inner member includes a first lumen and a second lumen is formed in the space between the inner member and the outer member. In this embodiment, the catheter may be configured to receive a guidewire in the first lumen of the inner member, wherein the guidewire would be inserted at the distal end 14 of the catheter and exit at the proximal end 12 of the catheter. Alternatively, the catheter may be constructed in a different manner wherein the guidewire would enter at the distal end 14 and exit along a length of the catheter distal to the proximal end 12, such a catheter design is typically referred to as rapid-exchange or RX.

A first expandable member 18 is disposed about the shaft 16 of the catheter adjacent to the distal end 14 of the shaft 16. The expandable member is preferably an inflatable balloon member. The first expandable member 18 is in fluid communication with a lumen of the shaft 16 as described above, wherein fluid may be passed through the lumen of the shaft into an interior space of the first expandable member, thereby causing the expandable member to expand from a first configuration to a second expanded configuration.

Figure 2A:
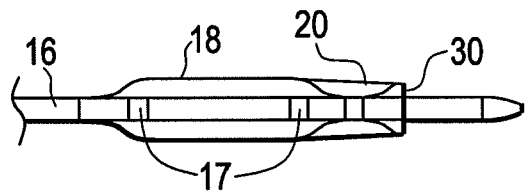
FIG. 2A is an enlarged view of the distal end portion of the catheter of FIG. 1.

A second expandable member 30 is disposed about the shaft 16 distal to the first expandable member 18a shown in FIG. 1. Unlike the first expandable member 18, the second expandable member 30 is configured to be self-expanding and does not require the application of force to expand. As shown in FIGS. 1 and 2A, a sheath 20 is disposed about the second expandable member 30 to retain the second expandable member in a contracted position to enable the catheter 10 to be disposed within a lumen of a vessel.

Figure 2B:
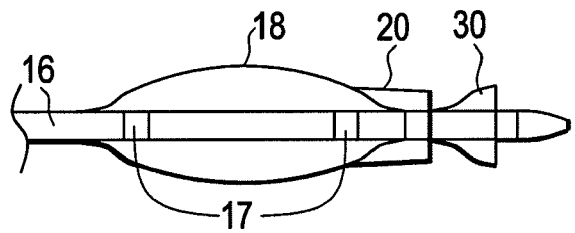
FIG. 2B is an enlarged view of the distal end portion of the catheter in accordance with the present invention illustrating the deployment of the second device.
Figure 2C:
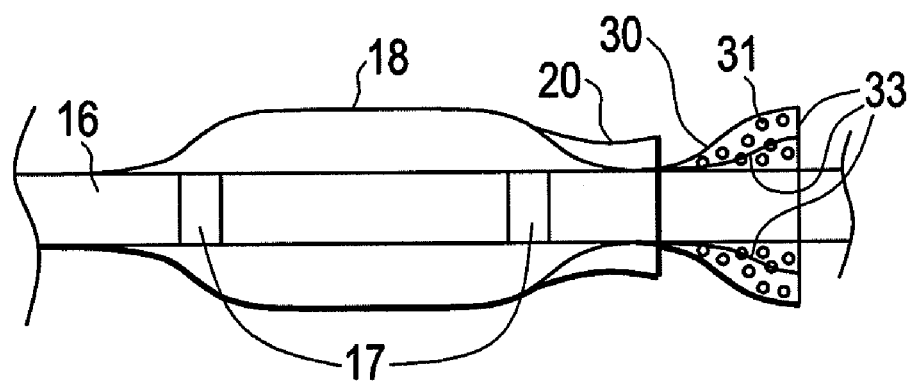
FIG. 2C is an enlarged view of the distal end portion of the catheter in accordance with the present invention illustrating an alternative embodiment of the second expandable member.

The second expandable member is preferably constructed of a material that is less stiff or has reduced hardness compared to those materials utilized for the construction of the other components of the catheter 10. The second expandable member 30 may further include a frame or strut members 33, as shown in FIG. 2C, disposed therein or thereupon or within to enable expansion of the member. For example, the second expandable member 30 may include one or more Nitinol wires associated therewith, wherein the Nitinol wires are configured to be disposed in a superelastic state or alternatively in a linear elastic state, thereby enabling expansion of the second expandable member.

As described above, a sheath 20 is disposed or at least partially disposed about the second expandable member 30 as shown in FIG. 2A, the sheath includes a proximal end 21 and a distal end 22. The proximal end 21 of the sheath 20 is affixed to either the shaft 16 of the catheter or to the first expandable member 18. The sheath 20 is configured to be slidably retracted over the second expandable member 30, thereby allowing the second expandable member to expand as shown in FIG. 2B. The sheath 20 is retracted from covering the second expandable member when the first expandable member is expanded as shown in FIG. 2B.

It is further contemplated that the second expandable member may comprise a porous membrane as shown in FIG. 2C, the pores indicated by reference number 31. The porous membrane allows fluid flow through the lumen to perfuse the emboli into the filter element as well as maintain flow within the lumen. Further still it is contemplated that the membrane may be formed having a helix pattern (not shown) on the proximal side thereof. The helix pattern would enable fluid flow past the second expandable member when in its deployed configuration.

Figure 2D:
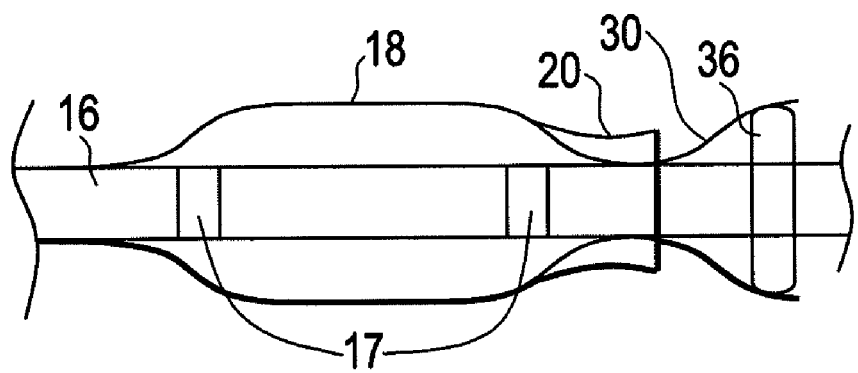
FIG. 2D is an enlarged view of the distal end portion of the catheter in accordance with the present invention illustrating another alternative embodiment of the second expandable member.

Referring now to FIG. 2D there is shown an exemplary embodiment of an alternative embodiment of the present invention. As shown in FIG. 2D, the second expandable member 30 may be constructed to include an inflatable member 36, thereby reducing the need for the sheath 20 to be disposed over the second expandable member 30. In this embodiment, the inflatable second inflatable member 36 would be associated with a second inflation lumen of the catheter shaft 16, thereby allowing a user to selectively inflate and deflate the member 36. In use, the second inflatable member 36 may remain inflated or may be deflated or partially deflated.

In yet another alternative embodiment shown in FIGS. 2E and 2F there are shown an alternative embodiments of the second expandable member, wherein the second expandable member comprises a bristle like structure composed of a plurality of members projecting from the shaft of the device 10 or from a guidewire 40 as described below.

Referring now to FIG. 2E there is shown yet another alternative embodiment of the alternative design of the second expandable member 300 of the present invention. As shown in FIG. 2E, the second expandable member is composed of a guidewire member 400, wherein a spiral pattern is cut into the wall of the shaft 16 of the medical device 10. In use, the inner guidewire 400 is rotated relative to the shaft 16, wherein the second ends of the members 320 are forced out through the spiral pattern 19 of the shaft 16. In this embodiment, the second expandable member 300 may be selectively expanded and contracted buy the user.

Referring now to FIG. 2F there is shown an exemplary embodiment of an alternative embodiment of the second expandable member of 300' of the present invention. As shown in FIG. 2F the bristles 320' may be disposed on a guidewire 40, wherein when the guidewire 40 is advanced distal to the distal end of the shaft 16, the bristles will expand from a collapsed configuration to an expanded configuration as shown in FIG. 2F. The guidewire can then be moved proximally either before or after deployment of a stent in the stenosed region of the vessel thereby liberating plaque from the lumen.

It is further contemplated in accordance with the present invention that the second expandable members described herein may be utilized in combination or separately during the methods of use in accordance with the present invention.

Figure 3:
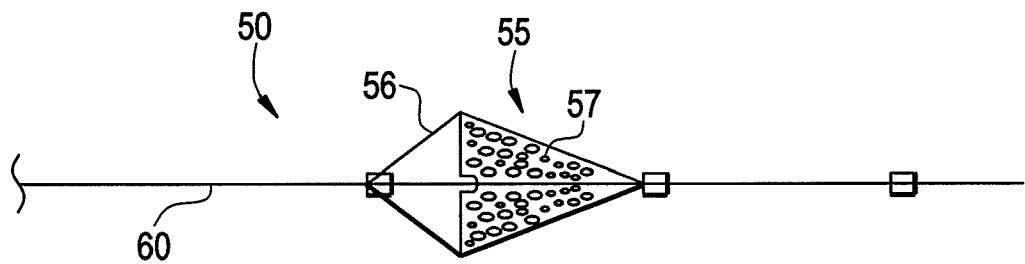
FIG. 3 is a plan view of an exemplary embodiment of an embolic protection device which may be utilized in combination with the catheter of the present invention.

Referring now to FIG. 3, there is shown an exemplary embodiment of an embolic protection device that may be utilized in combination with the catheter 10 of the present invention. As shown in FIG. 3, the embolic protection device 50 includes a guidewire 60 having a proximal and distal end and a filter member 55 disposed about the guidewire. The filter may be fixedly disposed or slidably disposed on the guidewire 60. The filter 55 includes a frame assembly 56 and a membrane 57 wherein the filter 55 is movable between a collapsed position (not shown) and an expanded position as shown. As described previously and shown in, for example, U.S. Pat. Nos. 6,336,934, 6,575,996, 6,695,813 and 7,097,440, the filter is delivered distal to the stenosed region in the collapsed configuration as known to one of ordinary skill in the art, the filter is then expanded to filter and capture emboli within the lumen from subsequent medical procedures.

Referring now to FIGS. 4 through 7 there is shown a cross-sectional view of a vessel, wherein the vessel includes a stenosed region R.

Figure 4:
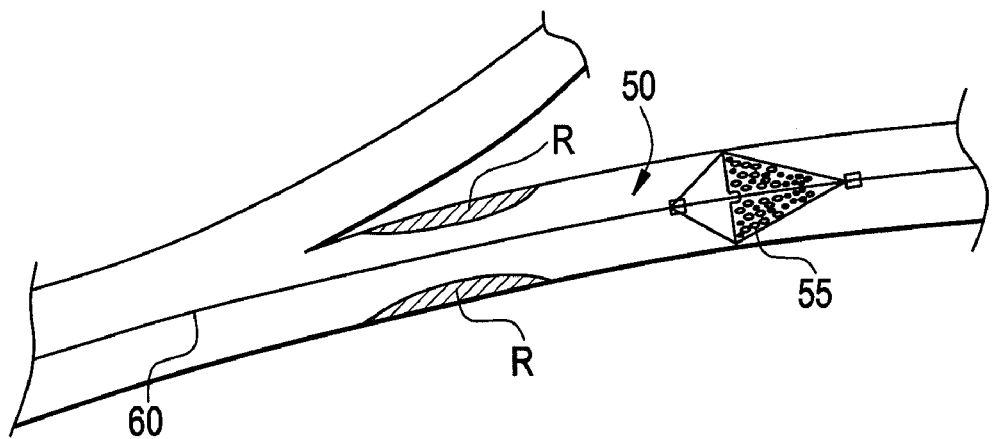
FIG. 4 is a cross-sectional view of a vessel illustrating an embolic protection device disposed distal a diseased portion of the vessel.

As shown in FIG. 4, an embolic protection device 50 such as that shown in FIG. 3 is has been disposed distal of the stenosed region R of the vessel. The filter 55 has been expanded from a first collapsed state to an expanded state. The guidewire 60 of the filter assembly passes proximally through the stenosed region R, thereby allowing subsequent medical devices to be passed over the wire into the stenosed region R for additional medical procedures to be performed.

Figure 5A:
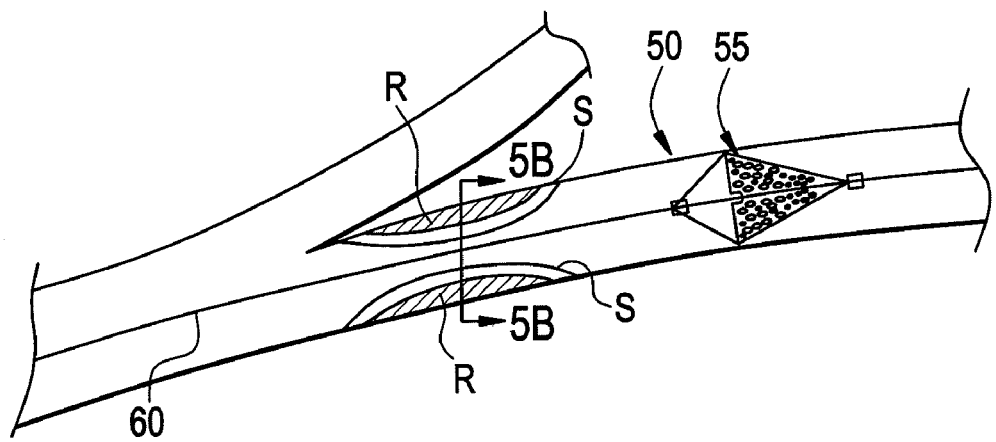
FIG. 5A illustrates a stent disposed within the diseased portion of the vessel.

As shown in FIG. 5A, a stent S has been delivered and deployed in the stenosed region R. The stent may be either a self-expanding stent or a balloon expandable stent and delivered using conventional stent implanting methods and procedures. The stent S may be an "open-cell" design, "closed-cell" design or a hybrid design containing both open- and closed-cell portions. Additionally, the stent may be constructed of a bioabsorbable material.

Figure 5B:
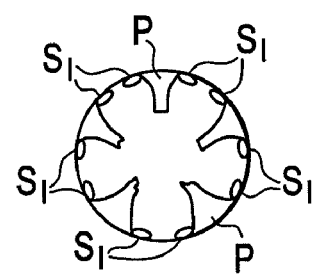
FIG. 5B is a cross-sectional view of the vessel taken about line 5B-5B of FIG. 5A, illustrating the plaque projecting into the lumen of the vessel after stenting.

Referring now to FIG. 5B there is shown a cross-sectional view taken about line 5B-5B of the stent S as implanted in the lumen as shown in FIG. 5A. As shown in FIG. 5B, the stent S is deployed against the wall of the lumen, wherein the struts of the stent S1 are placed against the wall to retain the diameter of the lumen while material such as plaque P extends into the lumen between the struts S1. It is this plaque P, that can later break off and float downstream which may cause blockage of other lumens which may then lead to adverse events such as stroke.

Figure 6:
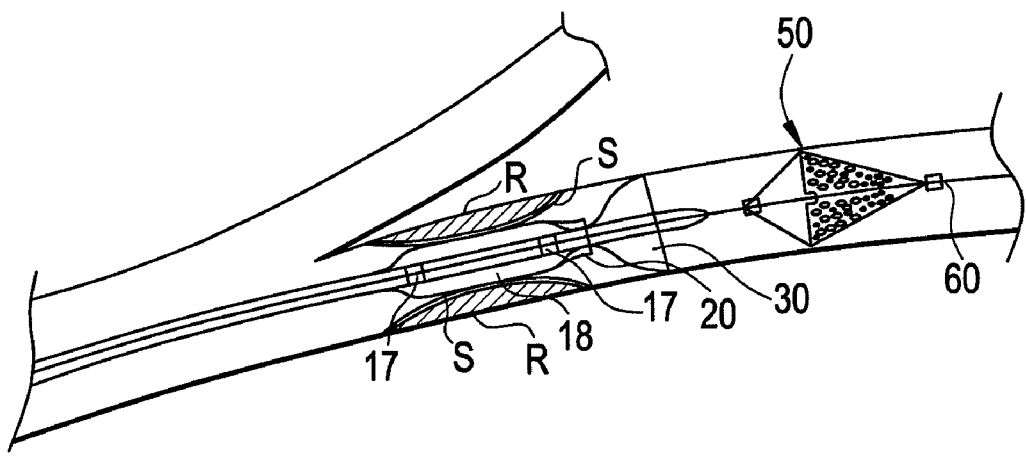
FIG. 6 illustrates the catheter of the present invention deployed for use.

Referring now to FIG. 6, the catheter 10 (or plaque liberating device) in accordance with the present invention is passed through the stent S, wherein the marker bands 17 of the catheter 10 are aligned such that the working area of the first expandable member 18 is aligned with the stent S. The first expandable member 18 is then expanded from the collapsed position to the expanded position. As the first expandable member 18 expands, the sheath 20 is retracted from covering the second expandable member 30, thereby allowing the second expandable member 30 to expand from the collapsed position to an expanded position. As shown in FIG. 6, the second expandable member 30 has a bell shape in the expanded position, wherein the enlarged portion of the bell is disposed distally. As described above, the second expandable member 30 is constructed of relatively soft materials and therefore will conform radially to the vessel or lumen in which it is disposed.

Figure 7:
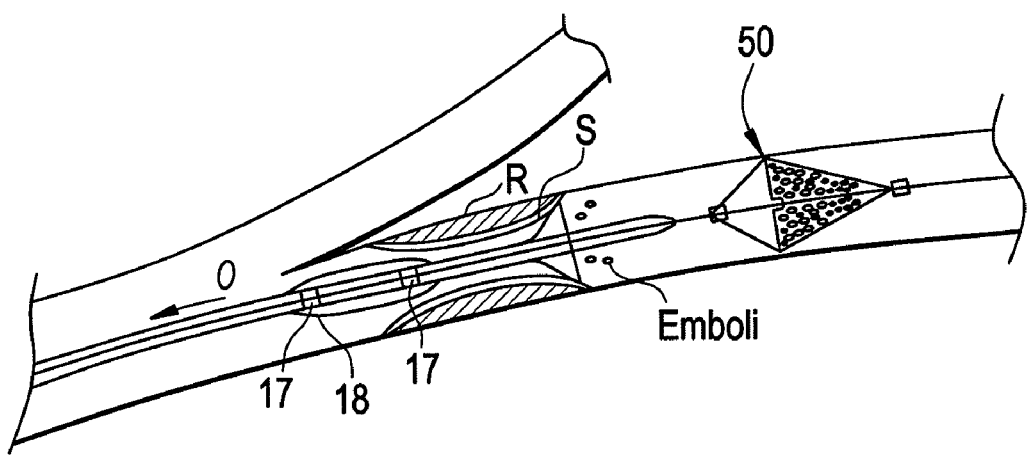
FIG. 7 illustrates the catheter of the present invention in use.

Referring now to FIG. 7, the catheter 10 is then moved distal to proximal O through the expanded stent S, the second expanded member 30 is pulled along the surface of the implanted stent S causing plaque or other material extending through the struts of the stent S to be scraped off as the catheter is moved proximally. As described above, the second expandable member 30 is constructed such that it is sufficiently soft and flexible so that when the catheter is moved proximally the second expandable member will flex along the length of the stent and struts and not cause the stent S to be moved within the vessel. As shown, the second expandable member 30 additionally temporarily blocks or restricts fluid flow within the vessel, whereby any particles loosened or broken free from the dragging motion of the second expandable member 30 will remain suspended in the vessel between the proximal end of the second expandable member 30 and the filter assembly 55.

Figure 8:
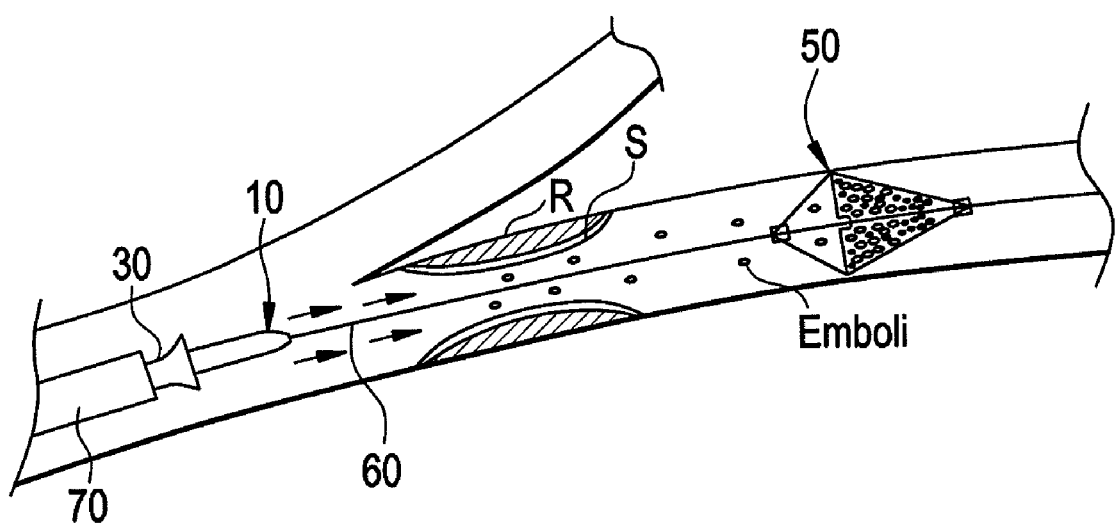
FIG. 8 illustrates embolic material being captured by the filter device disposed distal to the stent after usage device of the present invention.

Referring now to FIG. 8, after the second expandable member 30 and catheter 10 has been moved proximally through the entire length of the stent S, the catheter 10 including the second expandable member 30 may be retrieved with either a retrieval catheter (not shown) or alternatively moved proximally into a guiding catheter 70 which may have been used to access the treatment location. Once the catheter 10 and the second expandable member 30 have been moved into the retrieval catheter or guiding catheter 70, fluid flow within the lumen is restored. Any emboli or material that was knocked or scraped free by the second expandable member is captured by the filter 55 disposed distal to the stent S. After the emboli has been captured, the filter 55 can be retrieved using the necessary procedure to do so.

Regarding the alternative embodiments shown in FIGS. 2E and 2F, the methods of use are similar to those described above, wherein the second expandable members 300 and 300' would be deployed after the embolic protection device 50 has been deployed. The bristles 320 and 320' would be utilized to remove loose plaque or other embolic material from the lumen either before or after stenting.

The invention is susceptible to various modifications and alternative means, and specific examples thereof have been shown by way of example in the drawings and are herein described in detail. It should be understood, however, that the invention is not to be limited to the particular devices or methods disclosed, but to the contrary, the invention is to cover all modifications, equivalents, and alternatives falling within the spirit and scope of the claims.

What is claimed is:

1. A method for reducing emboli formation, comprising:
    inserting an embolic protection device within a lumen distal to an area of treatment, the embolic protection device including a guidewire;
    causing the embolic protection device to expand from a collapsed configuration to an expanded configuration;
    passing a medical device over the guidewire and performing a medical procedure in the area of treatment within the lumen adjacent to the embolic protection device;
    removing the medical device from the guidewire;
    passing a catheter over the guidewire, the catheter including first and second expandable members associated with the catheter, expanding the first expandable member thereby causing the second expandable member to expand;
    unexpanding the first expandable member and moving the catheter proximally from the area of treatment causing material extending into the vessel to be scraped off or knocked free by the expanded second expandable member; and
    retrieving the embolic protection device from the lumen.

2. The method according to claim 1, wherein the first expandable member is an inflatable balloon.

3. The method according to claim 2, wherein a sheath disposed at least partially about the second expandable member moves proximally, thereby uncovering the second expandable member, when the first expandable member is expanded.

4. The method according to claim 2, wherein expanding the first expandable member causes a sheath disposed at least partially about the second expandable member to move proximally, thereby uncovering the second expandable member.

5. The method according to claim 1, wherein the medical procedure is deploying a stent in the area to be treated.

6. The method according to claim 1, wherein the medical treatment is balloon angioplasty.

7. The method according to claim 1, wherein the embolic protection device is retrieved into a lumen of the catheter.

8. The method according to claim 1, wherein a sheath disposed at least partially about the second expandable member moves proximally to uncover and allow the expansion of the second expandable member.

9. The method according to claim 1, wherein the second expandable member includes a frame constructed of a superelastic material.

10. The method according to claim 9, wherein the second expandable member comprises a porous membrane supported by the frame.

11. The method according to claim 1, wherein the second expandable member comprises a bristle structure composed of a plurality of members projecting radially outwardly from a longitudinal delivery member.

12. The method according to claim 1, wherein the embolic protection device is an embolic protection filter comprising a frame assembly and a membrane.

13. A method for reducing emboli formation, comprising:
    delivering a guidewire through a vascular system of a patient;
    delivering an embolic protection filter element over the guidewire to a location within a blood vessel that is distal to a treatment location, the filter element being delivered in a collapsed position for movement through the vascular system;
    expanding the filter element to an expanded position in which the filter element at least partially contacts a wall of the blood vessel such that blood passing through the blood vessel travels through the filter element but embolic material in the blood is retained in the filter element;
    delivering a stent over the guidewire to the treatment location while the filter is in the expanded position, the stent being delivered in a collapsed position for movement through the vascular system;
    implanting the stent at the treatment location;
    delivering a plaque liberating device comprising an expandable member over the guidewire to a position distal the treatment location while the filter is in the expanded position;
    activating the plaque liberating device by expanding the expandable member;
    moving the activated plaque liberating device proximally through the implanted stent causing plaque or other material extending through the stent to be scraped off by the expandable member.

14. The method for reducing emboli formation according to claim 13, wherein the expanded expandable member will flex along the length of the stent and not cause the stent to be moved within the vessel.

15. The method for reducing emboli formation according to claim 13, wherein the expanded expandable member temporarily blocks or restricts fluid flow within the vessel.

16. The method for reducing emboli formation according to claim 15, wherein emboli or material dislodged by the expandable member will remain suspended in the vessel until the expandable member is collapsed.

17. The method for reducing emboli formation according to claim 13, wherein emboli or material dislodged by the expandable member is captured by the filter.

18. The method for reducing emboli formation according to claim 13, wherein a sheath disposed at least partially about the plaque liberating device is moved proximally to allow the expansion of the expandable member thereby activating the plaque liberating device.

19. The method for reducing emboli formation according to claim 13, wherein the plaque liberating devices includes a frame constructed of a superelastic material.

20. The method for reducing emboli formation according to claim 19, wherein the plaque liberating device includes a porous membrane supported by the frame.

21. The method for reducing emboli formation according to claim 13, wherein the plaque liberating device comprises a bristle structure composed of a plurality of members projecting radially outwardly from a longitudinal carrier.

22. The method for reducing emboli formation according to claim 21, wherein the longitudinal carrier is a guidewire and the plaque liberating device is activated by moving the guidewire relative to the plaque liberating device to expose and allow expansion of the bristle structure.

23. The method for reducing emboli formation according to claim 13, wherein the plaque liberating device is activated by expanding an inflatable balloon.

\* \* \* \* \*